(12) United States Patent
Lu et al.

(10) Patent No.: US 9,138,250 B2
(45) Date of Patent: Sep. 22, 2015

(54) MEDICAL INSTRUMENT HANDLE AND MEDICAL INSTRUMENT HAVING A HANDLE

(75) Inventors: Ifung Lu, Skokie, IL (US); Rudolph H. Nobis, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1725 days.

(21) Appl. No.: 11/409,709

(22) Filed: Apr. 24, 2006

(65) Prior Publication Data

US 2007/0250110 A1 Oct. 25, 2007

(51) Int. Cl.
*A61B 17/00* (2006.01)
*A61B 17/29* (2006.01)
*A61B 17/3205* (2006.01)

(52) U.S. Cl.
CPC ....... *A61B 17/2909* (2013.01); *A61B 17/32056* (2013.01); *A61B 2017/003* (2013.01)

(58) Field of Classification Search
CPC ............................. A61B 17/00; A61B 17/2841
USPC ........................................................... 606/1
See application file for complete search history.

(56) References Cited

U.S. PATENT DOCUMENTS

| | | |
|---|---|---|
| 1,225,771 A | 5/1917 | Clare |
| 2,976,865 A | 3/1961 | Shipley |
| 3,470,876 A | 10/1969 | Barchilon |
| 3,521,620 A | 7/1970 | Cook |
| 3,791,387 A | 2/1974 | Itoh |
| 3,799,151 A | 3/1974 | Fakaumi et al. |
| 3,805,791 A | 4/1974 | Seuberth et al. |
| 4,102,478 A | 7/1978 | Samoilov |
| 4,326,530 A | 4/1982 | Fleury, Jr. |
| 4,493,320 A | 1/1985 | Treat |
| 4,619,247 A | 10/1986 | Inoue et al. |
| 4,638,802 A | 1/1987 | Okada |
| 4,735,194 A | 4/1988 | Stiegmann |

(Continued)

FOREIGN PATENT DOCUMENTS

| | | |
|---|---|---|
| DE | 9300161 | 3/1993 |
| DE | 4408730 | 9/1995 |

(Continued)

OTHER PUBLICATIONS

Ginsberg, G.G., "Colonoscopy with the variable stiffness colonoscope," Gastrointestinal Endoscopy, vol. 58, No. 4 (2003).

(Continued)

*Primary Examiner* — Lynsey Crandall

(57) ABSTRACT

A medical instrument handle includes a stem, a joystick assembly, and a medical-instrument-member first articulation cable. The stem has a proximal stem portion and a distal stem portion. The joystick assembly includes a platform, a proximal joystick portion and a distal joystick portion, wherein the distal joystick portion is articulatably connected to the proximal stem portion. The first articulation cable includes a proximal cable portion which is connected to the platform and which is substantially transversely constrained by the stem. Articulation of the joystick assembly with respect to the stem changes a distance between the platform and the stem as measured along the first articulation cable. A medical instrument includes a medical instrument handle and a medical end effector. Examples of medical end effectors include, without limitation, a medical grasper and a medical snare.

20 Claims, 11 Drawing Sheets

(56) References Cited

U.S. PATENT DOCUMENTS

| | | |
|---|---|---|
| 4,739,768 A | 4/1988 | Engelson |
| 4,758,750 A | 7/1988 | Itagaki et al. |
| 4,791,963 A | 12/1988 | Gronert et al. |
| 4,884,557 A | 12/1989 | Takehana et al. |
| 4,890,602 A | 1/1990 | Hake |
| 4,893,613 A | 1/1990 | Hake |
| 4,930,494 A | 6/1990 | Takehana et al. |
| 4,963,147 A | 10/1990 | Agee et al. |
| 5,002,041 A | 3/1991 | Chikama |
| 5,035,696 A | 7/1991 | Rydell |
| 5,066,295 A | 11/1991 | Kozak et al. |
| 5,078,716 A | 1/1992 | Doll |
| 5,171,314 A | 12/1992 | Dulebohn |
| 5,201,732 A | 4/1993 | Parins et al. |
| 5,201,741 A | 4/1993 | Dulebohn |
| 5,250,060 A | 10/1993 | Carbo et al. |
| 5,293,869 A * | 3/1994 | Edwards et al. ............. 600/375 |
| 5,322,505 A | 6/1994 | Krause et al. |
| 5,342,299 A | 8/1994 | Snoke et al. |
| 5,346,504 A | 9/1994 | Ortiz et al. |
| 5,351,692 A | 10/1994 | Dow et al. |
| 5,353,807 A | 10/1994 | DeMarco |
| 5,397,304 A * | 3/1995 | Truckai ......................... 604/528 |
| 5,409,453 A | 4/1995 | Lundquist et al. |
| 5,431,671 A | 7/1995 | Nallakrishnan |
| 5,433,721 A | 7/1995 | Hooven et al. |
| 5,438,975 A | 8/1995 | Miyagi et al. |
| 5,441,499 A | 8/1995 | Fritzch |
| 5,482,029 A | 1/1996 | Sekiguchi et al. |
| 5,522,829 A | 6/1996 | Michalos |
| 5,531,664 A | 7/1996 | Adachi et al. |
| 5,531,686 A | 7/1996 | Lundquist et al. |
| 5,542,948 A | 8/1996 | Weaver et al. |
| 5,578,048 A | 11/1996 | Pasqualucci et al. |
| 5,618,294 A * | 4/1997 | Aust et al. ..................... 606/170 |
| 5,628,719 A | 5/1997 | Hastings et al. |
| 5,643,294 A | 7/1997 | Tovey et al. |
| 5,706,827 A | 1/1998 | Ehr et al. |
| 5,728,044 A | 3/1998 | Shan |
| 5,749,828 A | 5/1998 | Solomon et al. |
| 5,752,961 A | 5/1998 | Hill |
| 5,776,080 A | 7/1998 | Thome et al. |
| 5,792,165 A | 8/1998 | Klieman et al. |
| 5,810,715 A | 9/1998 | Moriyama |
| 5,810,807 A | 9/1998 | Ganz et al. |
| 5,836,947 A | 11/1998 | Fleischman |
| 5,848,986 A | 12/1998 | Lundquist et al. |
| 5,865,724 A | 2/1999 | Palmer et al. |
| 5,897,554 A | 4/1999 | Chia et al. |
| 5,910,148 A | 6/1999 | Reimels et al. |
| 5,972,012 A | 10/1999 | Ream et al. |
| 6,066,102 A | 5/2000 | Townsend et al. |
| 6,066,145 A | 5/2000 | Wurster |
| 6,071,277 A | 6/2000 | Farley et al. |
| 6,074,408 A | 6/2000 | Freeman |
| 6,093,185 A | 7/2000 | Ellis et al. |
| 6,093,195 A | 7/2000 | Ouchi |
| 6,152,918 A | 11/2000 | Padilla et al. |
| 6,174,280 B1 | 1/2001 | Oneda et al. |
| 6,203,494 B1 | 3/2001 | Moriyama |
| 6,352,503 B1 | 3/2002 | Matsui et al. |
| 6,371,907 B1 | 4/2002 | Hasegawa et al. |
| 6,395,001 B1 | 5/2002 | Ellman et al. |
| 6,423,059 B1 | 7/2002 | Hanson et al. |
| 6,443,943 B1 | 9/2002 | Ouchi |
| 6,443,944 B1 | 9/2002 | Doshi et al. |
| 6,450,948 B1 | 9/2002 | Matsuura et al. |
| 6,451,014 B1 | 9/2002 | Wakikaido et al. |
| 6,454,703 B1 | 9/2002 | Ide |
| 6,454,758 B1 | 9/2002 | Thompson |
| 6,475,222 B1 | 11/2002 | Berg et al. |
| 6,482,149 B1 | 11/2002 | Torii |
| 6,488,658 B1 | 12/2002 | Long |
| 6,500,189 B1 | 12/2002 | Lang et al. |
| 6,569,105 B1 | 5/2003 | Kortenbach et al. |
| 6,579,300 B2 | 6/2003 | Griego et al. |
| 6,602,267 B2 | 8/2003 | Castaneda |
| 6,612,992 B1 | 9/2003 | Hossack et al. |
| 6,663,616 B1 * | 12/2003 | Roth et al. ..................... 606/1 |
| 6,663,625 B1 | 12/2003 | Ormsby et al. |
| 6,689,119 B1 | 2/2004 | Di Caprio et al. |
| 6,709,388 B1 | 3/2004 | Mosse et al. |
| 6,730,097 B2 | 5/2004 | Dennis |
| 6,743,240 B2 | 6/2004 | Smith et al. |
| 6,761,171 B2 | 7/2004 | Toti et al. |
| 6,764,441 B2 | 7/2004 | Chiel et al. |
| 6,866,626 B2 | 3/2005 | Long et al. |
| 6,916,284 B2 | 7/2005 | Moriyama |
| 7,060,024 B2 | 6/2006 | Long et al. |
| 7,060,025 B2 | 6/2006 | Long et al. |
| 7,066,879 B2 | 6/2006 | Fowler et al. |
| 7,093,518 B2 | 8/2006 | Gmeilbauer |
| 7,118,587 B2 | 10/2006 | Dycus et al. |
| 7,273,488 B2 | 9/2007 | Nakamura et al. |
| 7,441,507 B2 | 10/2008 | Teraura et al. |
| 7,799,050 B2 | 9/2010 | Hensley et al. |
| 2001/0029397 A1 | 10/2001 | Thompson |
| 2001/0037084 A1 | 11/2001 | Nardeo |
| 2002/0017515 A1 | 2/2002 | Obata et al. |
| 2002/0087208 A1 | 7/2002 | Koblish et al. |
| 2002/0095168 A1 | 7/2002 | Griego et al. |
| 2002/0120178 A1 | 8/2002 | Tartaglia et al. |
| 2002/0147445 A1 | 10/2002 | Farley et al. |
| 2002/0177802 A1 | 11/2002 | Moutafis et al. |
| 2003/0014051 A1 | 1/2003 | Woloszko |
| 2003/0032863 A1 | 2/2003 | Kazakevich |
| 2003/0045778 A1 | 3/2003 | Ohline et al. |
| 2003/0069474 A1 | 4/2003 | Couvillon, Jr. |
| 2003/0074014 A1 | 4/2003 | Castaneda |
| 2003/0109898 A1 | 6/2003 | Schwarz et al. |
| 2003/0125788 A1 | 7/2003 | Long |
| 2003/0153866 A1 | 8/2003 | Long et al. |
| 2003/0181785 A1 | 9/2003 | Viebach et al. |
| 2003/0195492 A1 | 10/2003 | Gobron et al. |
| 2003/0208219 A1 | 11/2003 | Aznoian et al. |
| 2004/0034343 A1 | 2/2004 | Gillespie et al. |
| 2004/0044350 A1 | 3/2004 | Martin et al. |
| 2004/0068291 A1 | 4/2004 | Suzuki |
| 2004/0092953 A1 | 5/2004 | Salameh et al. |
| 2004/0097919 A1 | 5/2004 | Wellman et al. |
| 2004/0143159 A1 * | 7/2004 | Wendlandt ..................... 600/114 |
| 2004/0143160 A1 | 7/2004 | Couvillon, Jr. |
| 2004/0193016 A1 | 9/2004 | Root et al. |
| 2004/0204645 A1 | 10/2004 | Saadat et al. |
| 2004/0230096 A1 | 11/2004 | Stefanchik et al. |
| 2005/0043743 A1 | 2/2005 | Dennis |
| 2005/0154164 A1 | 7/2005 | Tabata |
| 2005/0183733 A1 | 8/2005 | Kawano et al. |
| 2005/0203610 A1 | 9/2005 | Tzeng |
| 2005/0222587 A1 | 10/2005 | Jinno et al. |
| 2005/0234296 A1 | 10/2005 | Saadat et al. |
| 2005/0251197 A1 | 11/2005 | Hensley et al. |
| 2005/0272975 A1 | 12/2005 | McWeeney et al. |
| 2005/0273084 A1 * | 12/2005 | Hinman et al. ................ 606/1 |
| 2005/0273085 A1 | 12/2005 | Hinman et al. |
| 2006/0009711 A1 | 1/2006 | Gingrich et al. |
| 2006/0089627 A1 | 4/2006 | Burnett et al. |
| 2007/0149853 A1 | 6/2007 | Chang |
| 2007/0225562 A1 * | 9/2007 | Spivey et al. ................. 600/121 |

FOREIGN PATENT DOCUMENTS

| | | |
|---|---|---|
| DE | 19729499 | 1/1999 |
| EP | 0027704 | 4/1981 |
| EP | 0397489 | 11/1990 |
| EP | 1310206 | 5/2003 |
| EP | 1849421 | 10/2007 |
| JP | 59-181124 | 10/1984 |
| JP | 02-241428 | 9/1990 |
| JP | 03-073125 | 3/1991 |
| JP | 03-077531 | 4/1991 |
| JP | 03-092126 | 4/1991 |
| JP | 03-264040 | 11/1991 |
| JP | 05-038326 | 2/1993 |

(56) References Cited

FOREIGN PATENT DOCUMENTS

| | | |
|---|---|---|
| JP | 05-285091 | 11/1993 |
| JP | 06-114037 | 4/1994 |
| JP | 06-154153 | 6/1994 |
| JP | 06-181882 | 7/1994 |
| JP | 08-322786 | 12/1996 |
| JP | 11-188102 | 7/1999 |
| JP | 11-285497 | 10/1999 |
| JP | 11-313834 | 11/1999 |
| JP | 2000-051149 | 2/2000 |
| JP | 2000-051218 | 2/2000 |
| JP | 2001-124122 | 5/2001 |
| JP | 2001-170000 | 6/2001 |
| JP | 2002-000556 | 1/2002 |
| JP | 2002-301088 | 10/2002 |
| JP | 2002-360507 | 12/2002 |
| JP | 2003-210391 | 7/2003 |
| JP | 2003-250748 | 9/2003 |
| JP | 2003-260021 | 9/2003 |
| JP | 2003-275166 | 9/2003 |
| JP | 2003-284784 | 10/2003 |
| JP | 2004-154164 | 6/2004 |
| JP | 2004-180781 | 7/2004 |
| JP | 2004-187798 | 7/2004 |
| JP | 2004-251779 | 9/2004 |
| JP | 2005-103123 | 4/2005 |
| JP | 2005-111273 | 4/2005 |
| JP | 2005-508710 | 4/2005 |
| JP | 2005-126843 | 5/2005 |
| JP | 2005-185544 | 7/2005 |
| JP | 2005-185644 | 7/2005 |
| JP | 2006-000643 | 1/2006 |
| JP | 2006-102361 | 4/2006 |
| WO | WO 96/00030 | 1/1996 |
| WO | 96/10957 | 4/1996 |
| WO | WO 97/12557 | 4/1997 |
| WO | 97/35135 | 9/1997 |
| WO | 99/12489 | 3/1999 |
| WO | 01/08737 | 2/2001 |
| WO | 01/82814 | 11/2001 |
| WO | 01/93938 | 12/2001 |
| WO | 02/43797 | 6/2002 |
| WO | 03/053225 | 7/2003 |
| WO | 03/092476 | 11/2003 |
| WO | 2005/113051 | 12/2005 |
| WO | 2006/019291 | 2/2006 |
| WO | 2006/026687 | 3/2006 |
| WO | 2006/122279 | 11/2006 |

OTHER PUBLICATIONS

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," EndoscopY; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

Examination Report, European Application No. 07251728.7 (Dec. 17, 2008).

European Search Report, European Application No. 07251934 (2 pages) (dated Aug. 30, 2007).

CN, Notification of First Office Action, Chinese Application No. 200710104449.2 (Feb. 12, 2010).

AU, Office Action dated Feb. 3, 2012, Australian Application No. 2007201564.

CN, Office Action dated Nov. 21, 2011, Chinese Application No. 200710104449.2.

JP, Office Action dated Mar. 6, 2012, Japanese Application No. 2007-113144.

EP, Search Report, European Application No. 07251688 (completed Jul. 4, 2007; mailed Jul. 16, 2007).

EP, Search Report, European Application No. 07251717 (completed Jul. 4, 2007; mailed Jul. 16, 2007).

EP, Search Report, European Application No. 07251683 (completed Aug. 3, 2007; mailed Aug. 10, 2007).

EP, Search Report, European Application No. 07252011 (completed Aug. 10, 2007; mailed Aug. 20, 2007).

EP, Search Report, European Application No. 07251868 (completed Aug. 27, 2007; mailed Sep. 4, 2007).

CA, Examination Report, Canadian Application No. 2,585,783 (Oct. 23, 2013).

CN, Notification of 3rd Office Action, Chinese Application No. 200710104449.2 (Jul. 30, 2012).

EP, Examination Report, European Application No. 07251683.4 (Jun. 10, 2008).

\* cited by examiner

MEDICAL INSTRUMENT HANDLE AND MEDICAL INSTRUMENT HAVING A HANDLE

FIELD OF THE INVENTION

The present invention is related generally to medical equipment, and more particularly to a medical instrument handle and to a medical instrument having a handle.

BACKGROUND OF THE INVENTION

Endoscopes (including colonoscopes) are known which have an insertion tube which is insertable within a patient. The insertion tube has an articulatable distal end portion controlled by wires running from the distal end portion to control knobs on the handle of the endoscope. A wide angle video camera in the distal end of the insertion tube permits medical observation. Medical devices, such as a medical snare, are part of an endoscopic system and are insertable into the working channel(s) of the insertion tube of the endoscope and are translatable to extend from the distal end portion for medical treatment. Other medical devices are known which use a manually-pulled pull wire, surrounded by a flexible sheath connected to a handle, to articulate an end effector about a pivot pin.

Still, scientists and engineers continue to seek improved medical instrument handles and improved medical instruments having a handle.

SUMMARY OF THE INVENTION

A first expression of a first embodiment of the invention is for a medical instrument handle including a stem, a joystick assembly, and a medical-instrument-member first articulation cable. The stem has a proximal stem portion and a distal stem portion. The joystick assembly includes platform, a proximal joystick portion and a distal joystick portion, wherein the distal joystick portion is articulatably connected to the proximal stem portion. The first articulation cable includes a proximal cable portion which is connected to the platform and which is substantially transversely constrained by the stem. Articulation of the joystick assembly with respect to the stem changes a distance between the platform and the stem as measured along the first articulation cable.

A second expression of a first embodiment of the invention is for a medical instrument including a flexible tube, a medical end effector, a medical-end-effector activation wire, a fitting, a lengthwise-translatable first cable, and a handle. The tube has a distal tube portion insertable within a patient. The medical end effector is connected to the distal tube portion. The activation wire is positioned within the tube. The fitting is spaced apart from, and positioned proximal to, the medical end effector, wherein the fitting is attached to the tube. The first cable is positioned outside the tube, is substantially transversely constrained by the fitting, and has a distal cable portion attached to the medical end effector. Lengthwise translation of the first cable articulates the medical end effector with respect to the fitting. The handle includes a stem and a joystick assembly. The stem has a proximal stem portion and a distal stem portion. The joystick assembly includes a platform, a proximal joystick portion and a distal joystick portion, wherein the distal joystick portion is articulatably connected to the proximal stem portion. The first cable includes a proximal cable portion which is connected to the platform and which is substantially transversely constrained by the stem. Articulation of the joystick assembly with respect to the stem changes a distance between the platform and the stem as measured along the first cable.

A first expression of a second embodiment of the invention is for a medical instrument including a flexible tube, a coupling, a medical end effector, an activation wire, a fitting, a lengthwise-translatable first cable, and a handle. The tube defines a passageway and has a distal tube portion insertable within a patient. The coupling is connected to the distal tube portion and has a lumen in communication with the passageway. The medical end effector is positionable in the lumen of the coupling. The activation wire is positionable in the passageway and is connected to the medical end effector. The fitting is spaced apart from, and positioned proximal to, the coupling, wherein the fitting is attached to the tube. The first cable is positioned outside the tube, is substantially transversely constrained by the fitting, and has a distal cable portion attached to the coupling. Lengthwise translation of the first cable articulates the coupling with respect to the fitting. The handle includes a stem and a joystick assembly. The stem has a proximal stem portion and a distal stem portion. The joystick assembly includes a platform, a proximal joystick portion and a distal joystick portion, wherein the distal joystick portion is articulatably connected to the proximal stem portion. The first cable includes a proximal cable portion which is connected to the platform and which is substantially transversely constrained by the stem. Articulation of the joystick assembly with respect to the stem changes a distance between the platform and the stem as measured along the first cable.

Several benefits and advantages are obtained from one or more of the expressions of the embodiments of the invention. In a first example, the joystick assembly of the medical instrument handle, with multiple cables, offers intuitive operation of the handle to provide articulation of a medical instrument member (such as, without limitation, a medical end effector or a coupling having a lumen in which a medical end effector is positionable) which is not limited to a single plane.

DETAILED DESCRIPTION OF THE INVENTION

Figure 1:
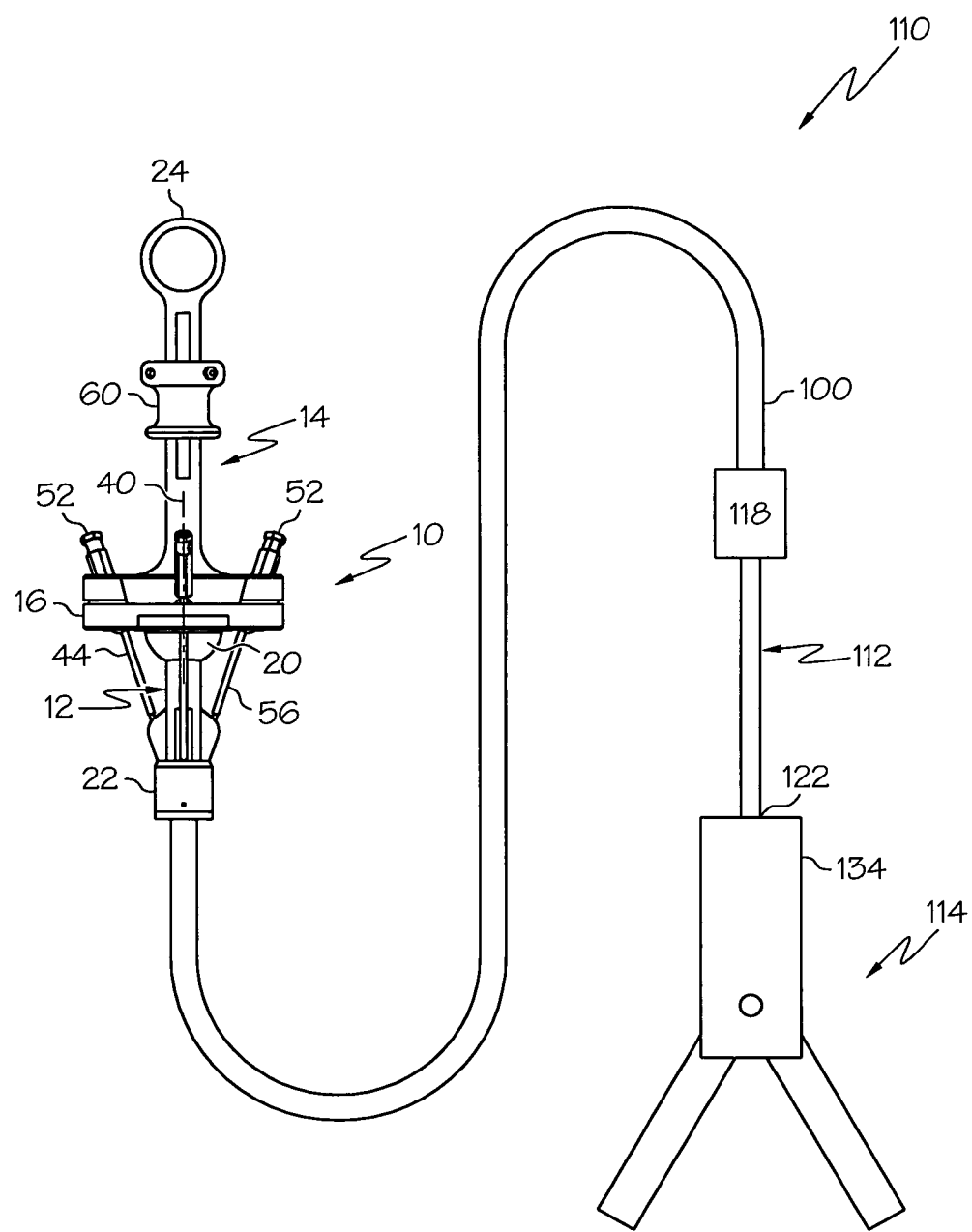
FIG. 1 is a schematic side elevational view of a first embodiment of a medical instrument of the invention including an embodiment of a medical instrument handle, wherein the cables have been omitted for clarity.
Figure 2:
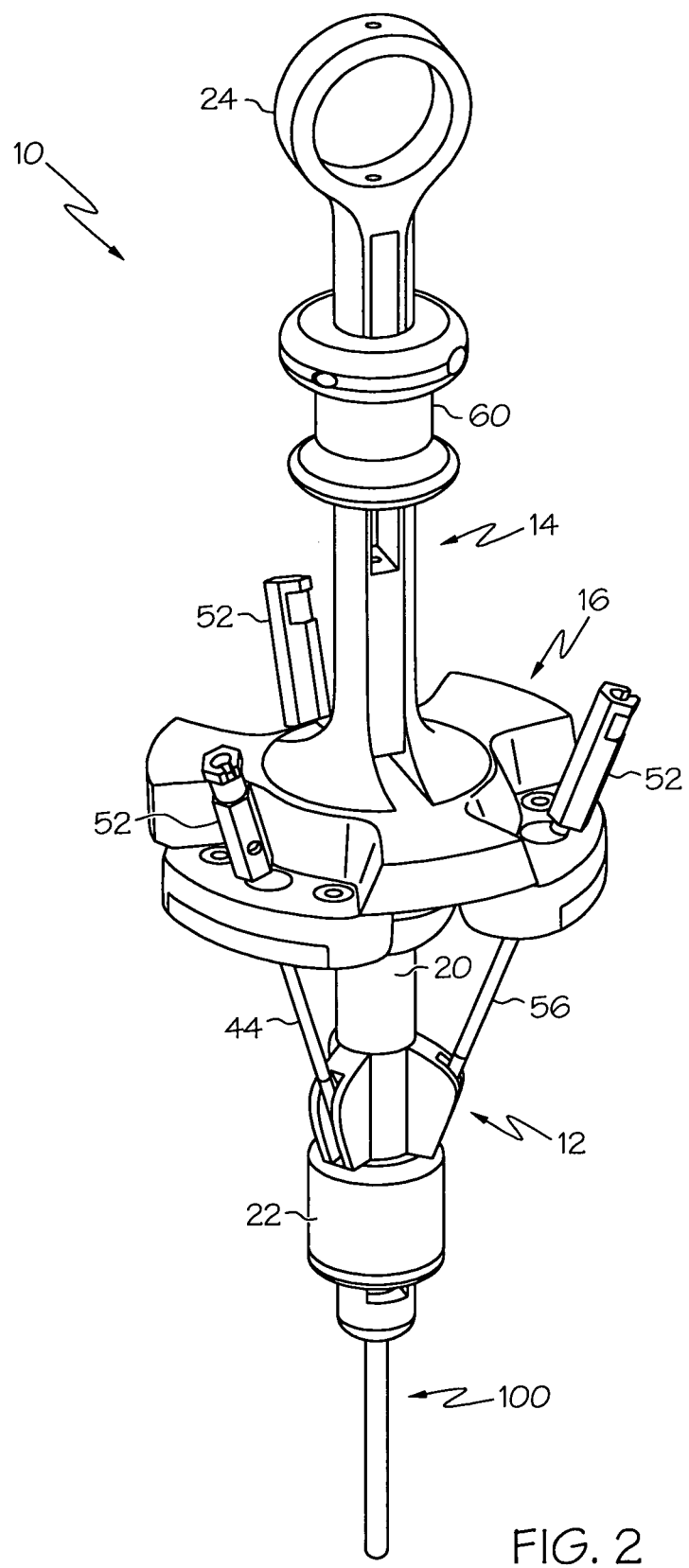
FIG. 2 is a schematic perspective view of the embodiment of the medical instrument handle of FIG. 1.
Figure 3:
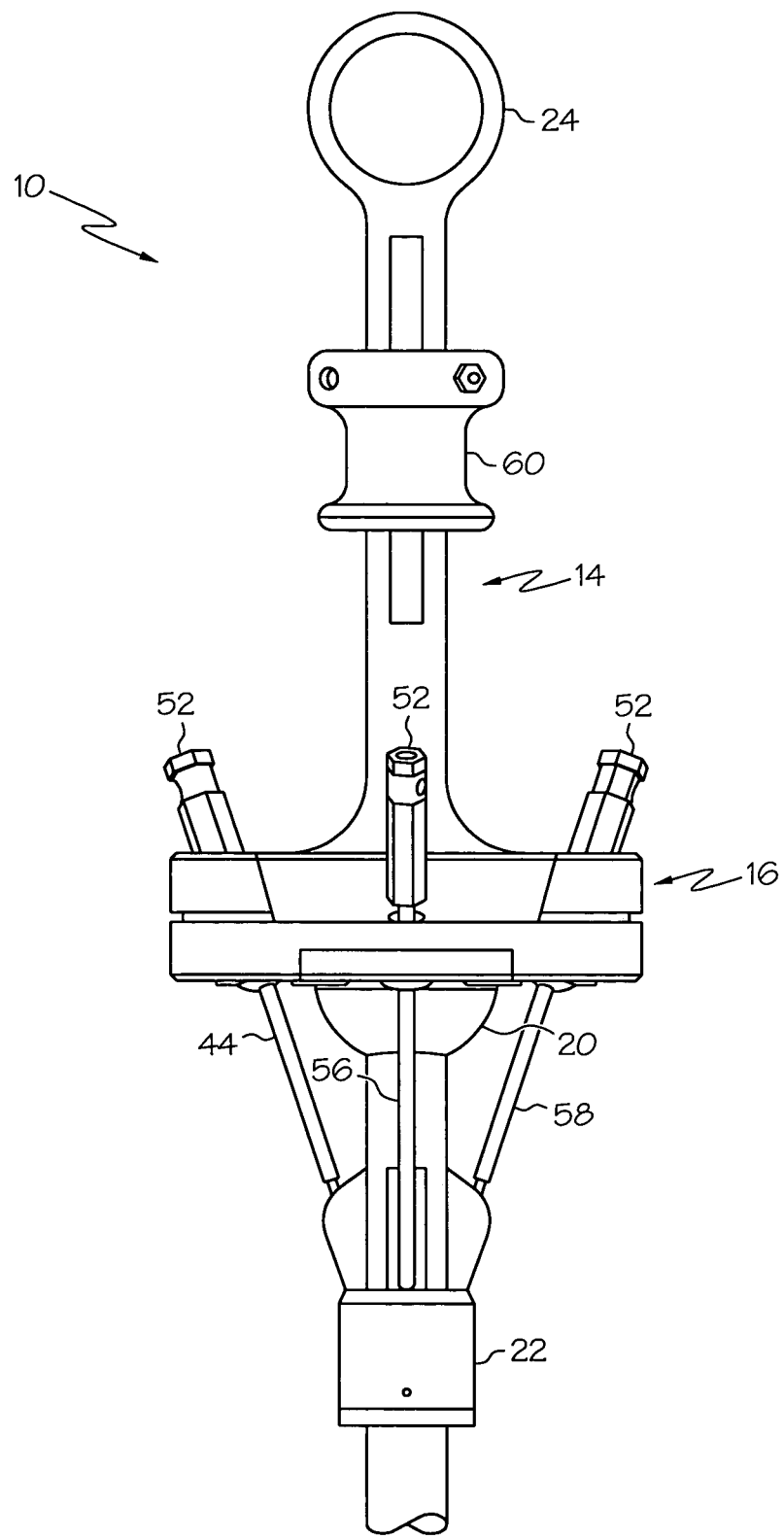
FIG. 3 is a side elevational view of a portion of the medical instrument handle of FIG. 2.
Figure 4:
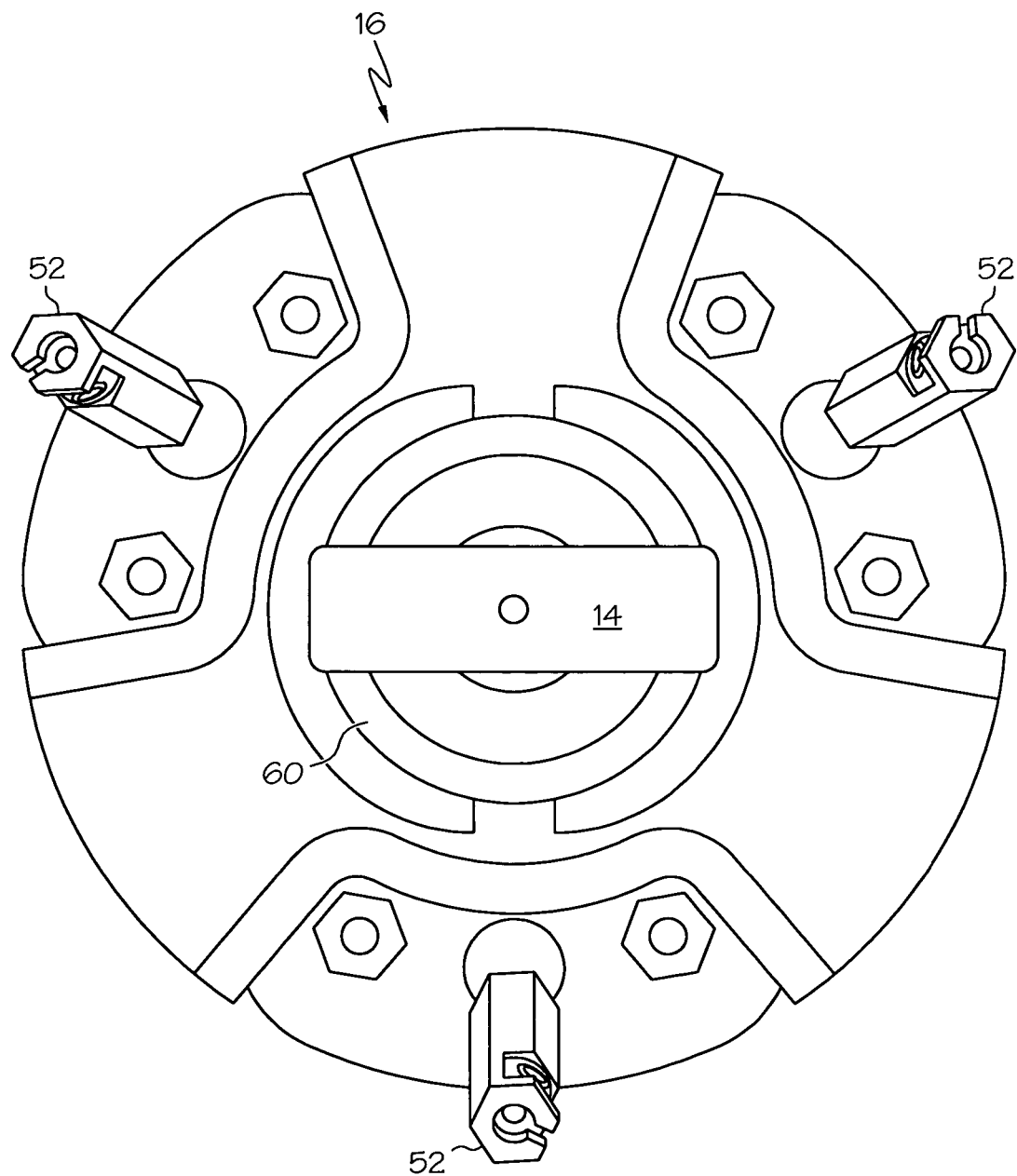
FIG. 4 is a top planar view of the medical instrument handle of FIG. 2.
Figure 5:
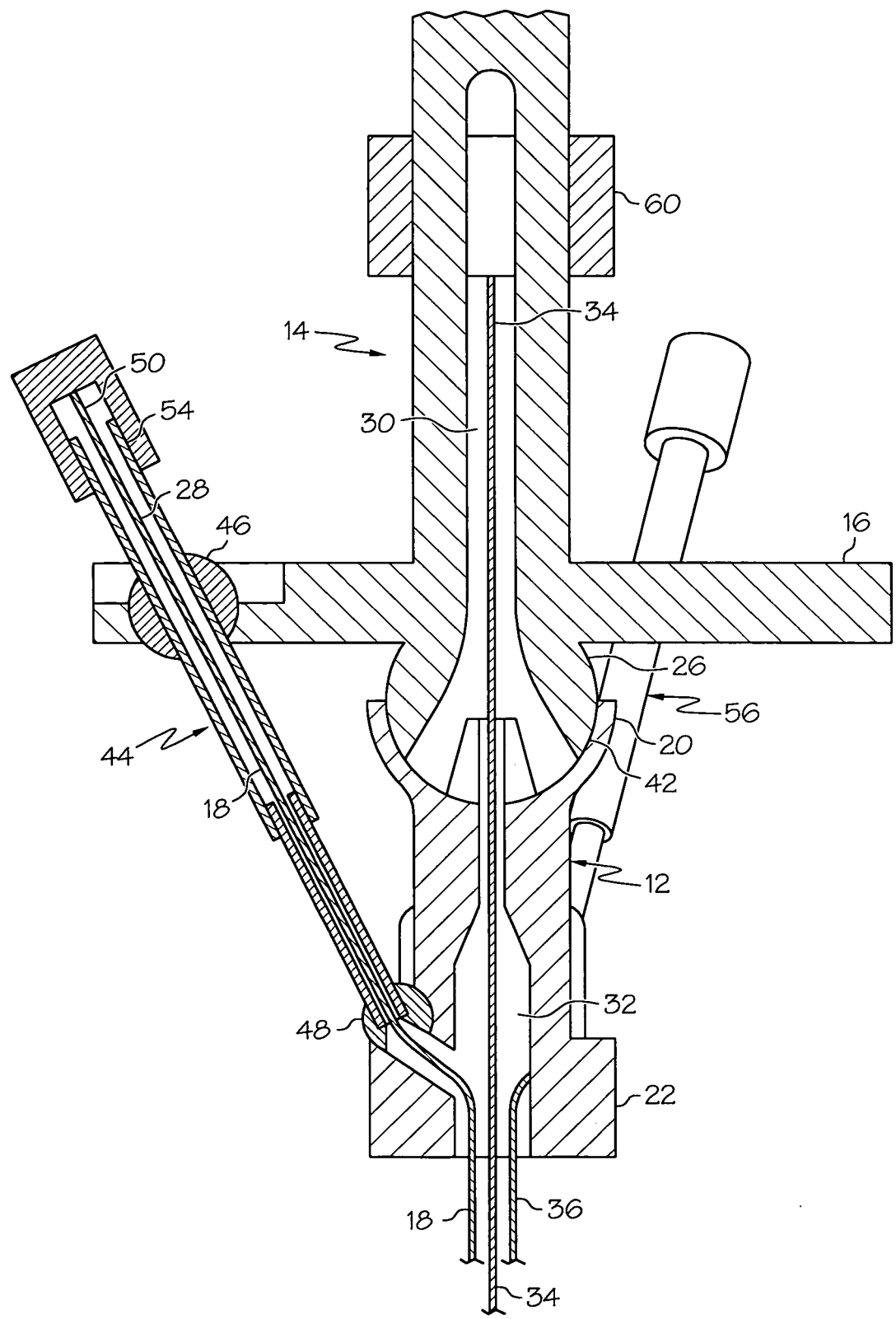
FIG. 5 is a schematic, cross sectional view of a portion of FIG. 3 showing the ball and socket attachment of the joystick assembly to the stem and showing the medical-instrument-member first articulation cable connected to the platform, wherein the tube surrounding the first articulation cable has been omitted for clarity.
Figure 6:
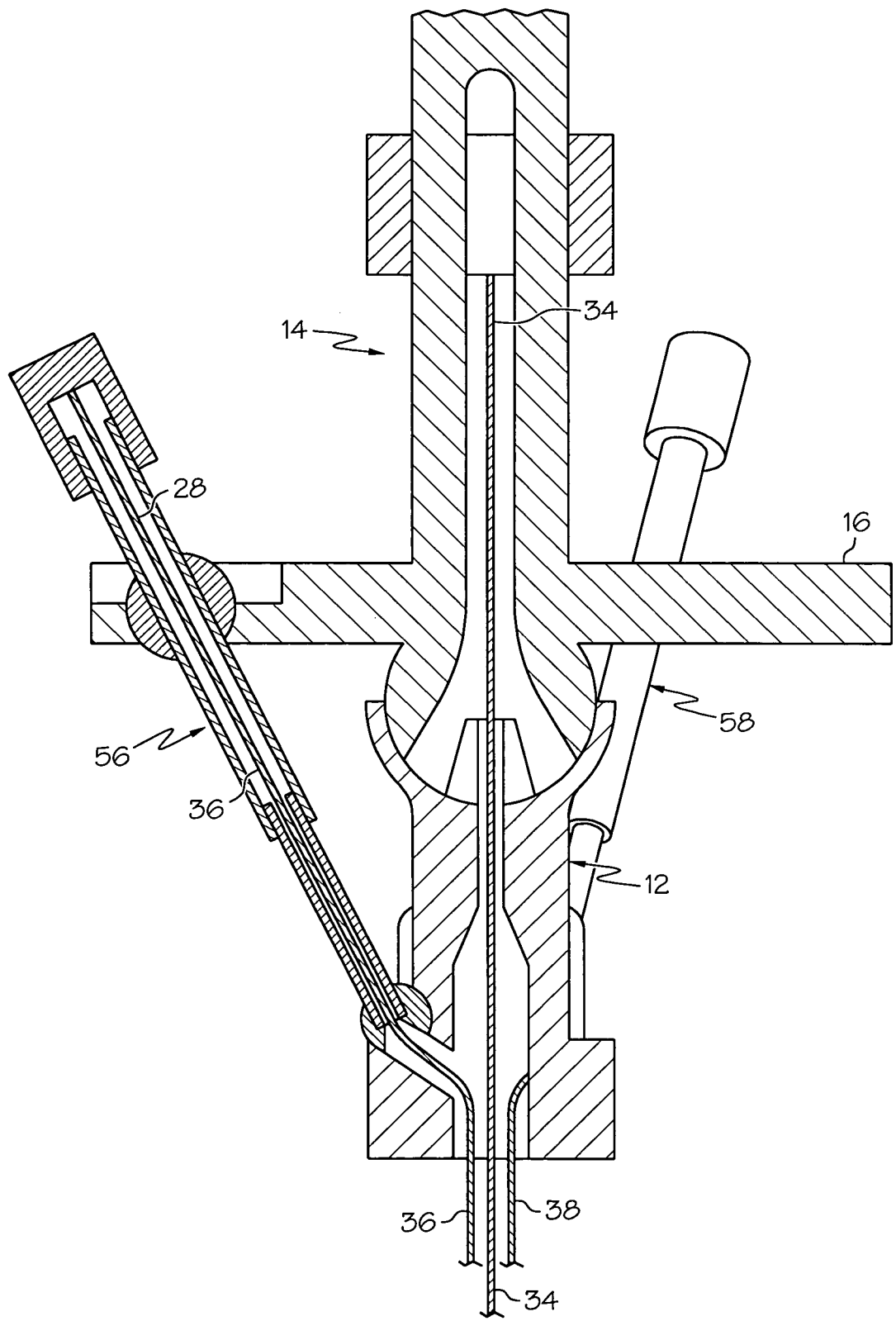
FIG. 6 is a view, as in FIG. 5, but from a different angle showing the medical-instrument-member second articulation cable connected to the platform.
Figure 7:
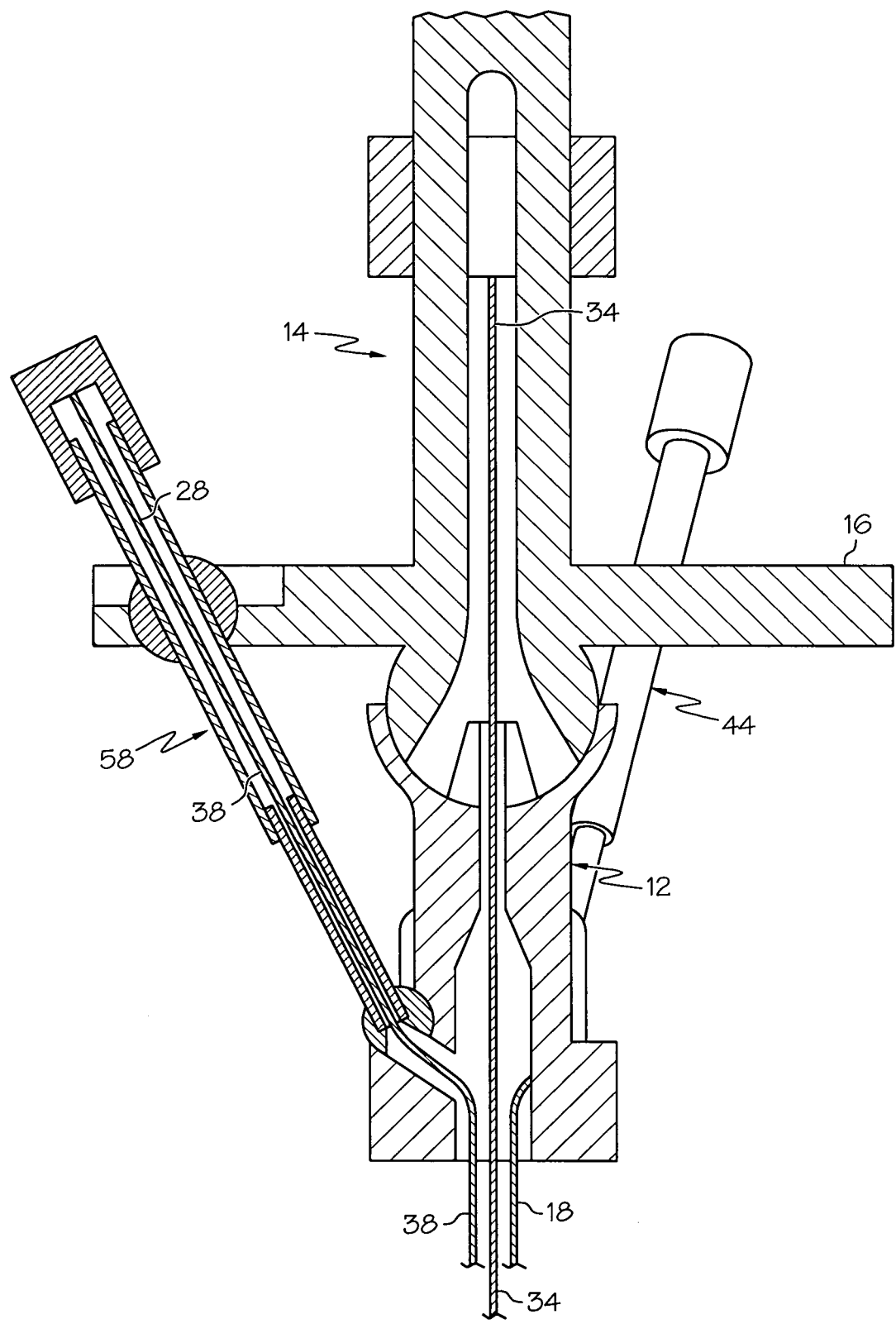
FIG. 7 is a view, as in FIG. 5, but from a different angle showing the medical-instrument-member third articulation cable connected to the platform.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Referring now to the Figures, wherein like numerals represent like elements throughout, FIGS. 1-9 illustrate a first embodiment of the invention. A first expression of the embodiment of FIGS. 1-9 is for a medical instrument handle (also called a handle) 10 including a stem 12, a joystick assembly 14, and a medical-instrument-member first articulation cable (also called a first cable) 18. The stem 12 has a proximal stem portion 20 and a distal stem portion 22. The joystick assembly 14 includes a platform 16, a proximal joystick portion 24 and a distal joystick portion 26, wherein the distal joystick portion 26 is articulatably connected to the proximal stem portion 20. The first articulation cable 18 includes a proximal cable portion 28 which is connected to the platform 16 and which is substantially transversely constrained by the stem 12. Articulation of the joystick assembly 14 with respect to the stem 12 changes a distance between the platform 16 and the stem 12 as measured along the first articulation cable 18. It is noted that the term "cable" includes any elongated member adapted for lengthwise translating a force such as, without limitation, a wire such, without limitation, as a wire comprising, consisting essentially of, or consisting of nitinol.

In one enablement of the first expression of the embodiment of FIGS. 1-9, the joystick assembly 14 has a joystick lumen 30 and the stem 12 has a stem lumen 32 in communication with the joystick lumen 30. In one variation, the medical instrument handle also includes a medical-end-effector activation wire (also called an activation wire) 34 disposed in the joystick lumen 30 and in the stem lumen 32.

In a one extension of the first expression of the embodiment of FIGS. 1-9, the medical instrument handle 10 also includes a medical-instrument-member second articulation cable 36 including a proximal cable portion 28 which is connected to the platform 16 and which is substantially transversely constrained by the stem 12, wherein articulation of the joystick assembly 14 with respect to the stem 12 changes a distance between the platform 16 and the stem 12 as measured along the second articulation cable 36. In one variation, the medical instrument handle 10 also includes a medical-instrument-member third articulation cable 38 including a proximal cable portion 28 which is connected to the platform 16 and which is substantially transversely constrained by the stem 12, wherein articulation of the joystick assembly 14 with respect to the stem 12 changes a distance between the platform 16 and the stem 12 as measured along the third articulation cable 38. In one modification, the platform 16 has a longitudinal axis 40, and the proximal cable portions 28 of the first, second and third articulation cables 18, 36 and 38 are substantially circularly arrayed 120 degrees apart from each other about the longitudinal axis 40.

In a first implementation of the first expression of the embodiment of FIGS. 1-9, the distal joystick portion 26 is articulatably connected to the proximal stem portion 20 with a ball-and-socket attachment 42. In a second implementation, not shown, the distal joystick portion is articulatably connected to the proximal stem portion with a universal joint. Single plane, and other multiple plane, articulatable connections are left to those skilled in the art. In one construction, the platform 16 is disposed 16 proximate the distal joystick portion 26.

In one illustration of the first expression of the embodiment of FIGS. 1-9, the medical instrument handle 10 also includes a first conduit 44 which surrounds the first articulation cable 18 and which is connected to the platform 16 and to the stem 12. In one variation, the first conduit 44 is a telescoping conduit. In one example, the first conduit 44 is connected to the platform 16 by a ball-and-socket connection 46 and to the stem 12 by a ball-and-socket connection 48.

In one configuration of the first expression of the embodiment of FIGS. 1-9, the proximal cable portion 28 has a proximal cable end 50, wherein the first articulation cable 18 has a first distance between the proximal cable end 50 and the platform 16, and the first distance is adjustable. In one variation, an adjustment nut 52 is threadably attached to the proximal end portion 54 of the first conduit 44, and the proximal cable end 50 is attached to the adjustment nut 52. In one extension, the medical instrument handle 10 also includes a second conduit 56 which surrounds the second articulation cable 36 and includes a third conduit 58 which surrounds the third articulation cable 38 in a like manner as the first conduit 44 surrounds the first articulation cable 18 and with like conduit connections and cable length adjustments.

A second expression of the embodiment of FIGS. 1-9 is for a medical instrument 110 including a flexible tube 112, a medical end effector 114, a medical-end-effector activation wire 34, a fitting 118, a lengthwise translatable first cable 18, and a handle 10. The flexible tube 112 has a distal tube portion 122 insertable within a patient. The medical end effector 114 is connected to the distal tube portion 122. The activation wire 34 is disposed within the tube 112. The fitting 118 is spaced apart from, and is disposed proximal to, the medical end effector 114. The fitting 118 is attached to the tube 112. The first cable 18 is disposed outside the tube 112, is substantially transversely constrained by the fitting 118, and has a distal cable portion 124 attached to the medical end effector 114. Lengthwise translation of the first cable 18 articulates the medical end effector 114 (which is a medical instrument member) with respect to the fitting 118. The handle 10 includes a stem 12 and a joystick assembly 14. The stem 12 has a proximal stem portion 20 and a distal stem portion 22. The joystick assembly 14 includes a platform 16, a proximal joystick portion 24 and a distal joystick portion 26, wherein the distal joystick portion 26 is articulatably connected to the proximal stem portion 20. The first cable 18 includes a proximal cable portion 28 which is connected to the platform 16 and which is substantially transversely constrained by the stem 12. Articulation of the joystick assembly 14 with respect to the stem 12 changes a distance between the platform 16 and the stem 12 as measured along the first cable 18. It is noted that such articulation of the joystick assembly 14 results in articulation of the medical end effector 114 with respect to the fitting 118.

Figure 8:
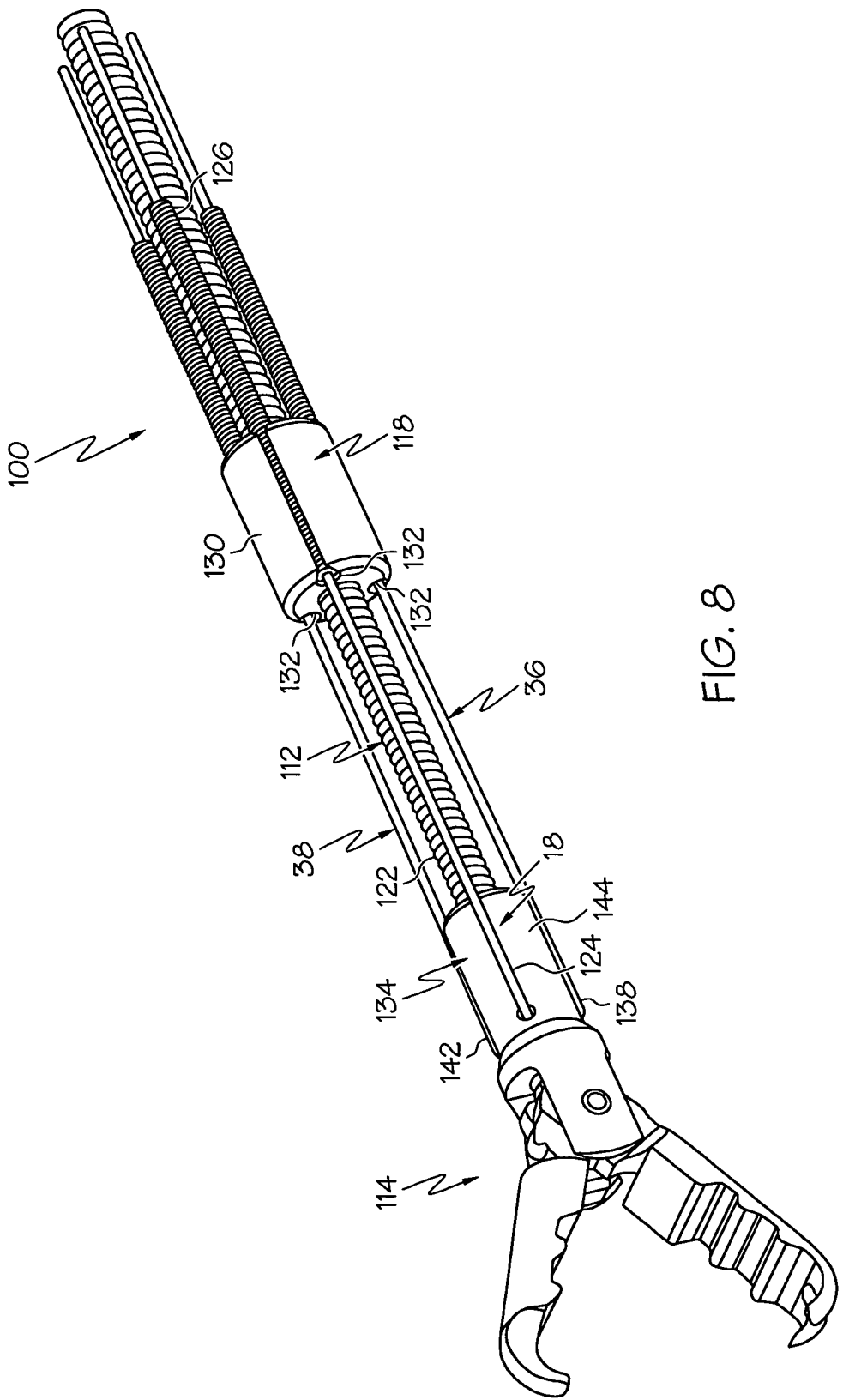
FIG. 8 is an enlarged view of a distal portion of the medical instrument of FIG. 1, wherein pulling of at least one cable articulates the medical end effector, and wherein the medical end effector is a medical grasper.

It is noted that an example of a tubular assembly 100 extending from the stem 12 to the fitting 118 is shown in FIG. 1, such tubular assembly 100 being shown in more detail in FIG. 8 wherein it is understood that in FIG. 8 the pipes (such as the first pipe 126) would extend to the stem 12.

In one enablement of the second expression of the embodiment of FIGS. 1-9, the joystick assembly 14 has a joystick lumen 30 and the stem 12 has a stem lumen 32 in communication with the joystick lumen 30. In one variation, the activation wire 34 is disposed in the joystick lumen 30 and in the stem lumen 32.

In a first extension of the second expression of the embodiment of FIGS. 1-9, the medical instrument 110 also includes a lengthwise translatable second cable 36 disposed outside the tube 112, substantially transversely constrained by the fitting 118, and having a distal cable portion 138 attached to the medical end effector 114. Lengthwise translation of the second cable 36 articulates the medical end effector 114 with respect to the fitting 118. The second cable 36 includes a proximal cable portion 28 which is connected to the platform 16 and which is substantially transversely constrained by the stem 12. Articulation of the joystick assembly 14 with respect to the stem 12 changes a distance between the platform 16 and the stem 12 as measured along the second cable 36. In one variation, the medical instrument 110 also includes a lengthwise translatable third cable 38 disposed outside the tube 112, substantially transversely constrained by the fitting 118, and having a distal cable portion 138 attached to the medical end effector 114. Lengthwise translation of the third cable 38 articulates the medical end effector 114 with respect to the fitting 118. The third cable 38 includes a proximal cable portion 28 which is connected to the platform 16 and which is substantially transversely constrained by the stem 12. Articulation of the joystick assembly 14 with respect to the stem 12 changes a distance between the platform 16 and the stem 12 as measured along the third cable 38. In one modification, the platform 16 has a longitudinal axis 40, and the proximal cable portions 28 of the first, second and third cables 18, 36 and 38 are substantially circularly arrayed 120 degrees apart from each other about the longitudinal axis 40.

Figure 9:
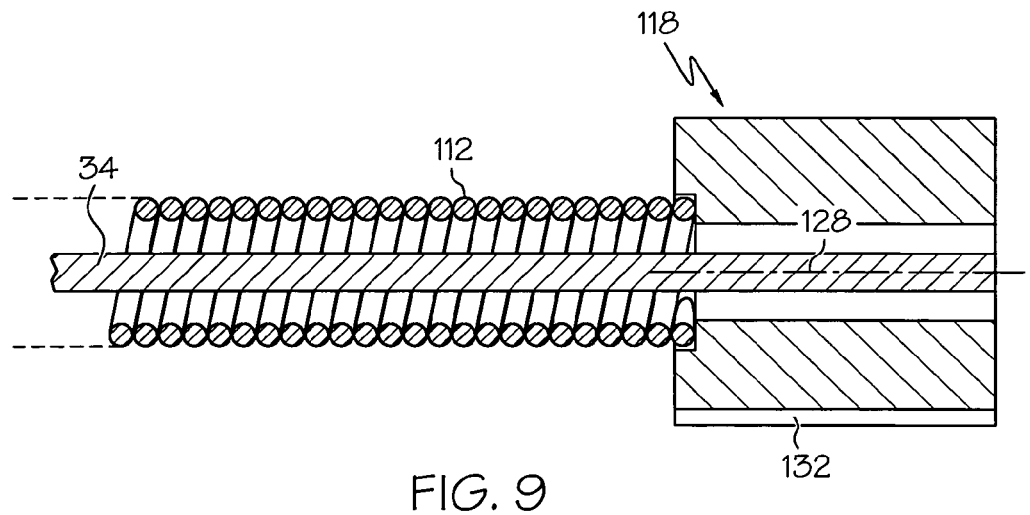
FIG. 9 is a side elevational, cross sectional view of the fitting and a portion of the tube of FIG. 8.

In one implementation of the second expression of the first embodiment of FIGS. 1-9, the medical instrument 110 also includes a flexible first pipe 126 surrounding the first cable 18 and attached to the fitting 118. In one variation, the first pipe 126 does not extend distally of the fitting 118. In the same or a different variation, the first pipe 126 is a first coil pipe. In the same or a different variation, the fitting 118 has a longitudinal axis 128, and the tube 112 is substantially coaxially aligned with the longitudinal axis 128 within the fitting 118. In one modification, the fitting 118 has a longitudinally-extending circumferential surface 130, and the first pipe 126 is disposed in a surface groove 132 (three grooves are shown in FIG. 8 and one groove is shown in FIG. 9) of the circumferential surface 130 of the fitting 118. In one example, the tube 112 is a coil-pipe tube. In a first employment, adjacent coil turns of a coil pipe are in contact with each other. In a second employment, adjacent coil turns of a coil pipe are spaced apart from each other.

In a first construction of the second expression of the first embodiment of FIGS. 1-9, the medical end effector 114 has a proximal end-effector portion 134, and the first cable 18 is attached to the proximal end-effector portion 134 of the medical end effector 114. In one variation, the fitting 118 has a first diameter, and the proximal end-effector portion 134 has a second diameter which is substantially equal to the first diameter. In the same or a different variation, the tube 112 has a diameter which is smaller than the first diameter distal of the fitting 118.

Examples, without limitation, of medical end effectors 114 of the second expression of the embodiment of FIGS. 1-9, include a medical grasper (as shown in FIGS. 1 and 8) and include medical forceps (not shown). Other examples are left to the artisan. In the example of the medical grasper, the distal end of the activation wire 34 is operatively connected to the jaw opening and closing mechanism of the medical grasper as is well known in the art. In one variation, the handle 10 includes a knob 60 attached to the proximal end of the activation wire 34, wherein the knob 60 surrounds, and is slidably mounted on, the joystick 14, and wherein sliding the knob 60 opens and closes the jaws of the medical grasper.

Figure 12:
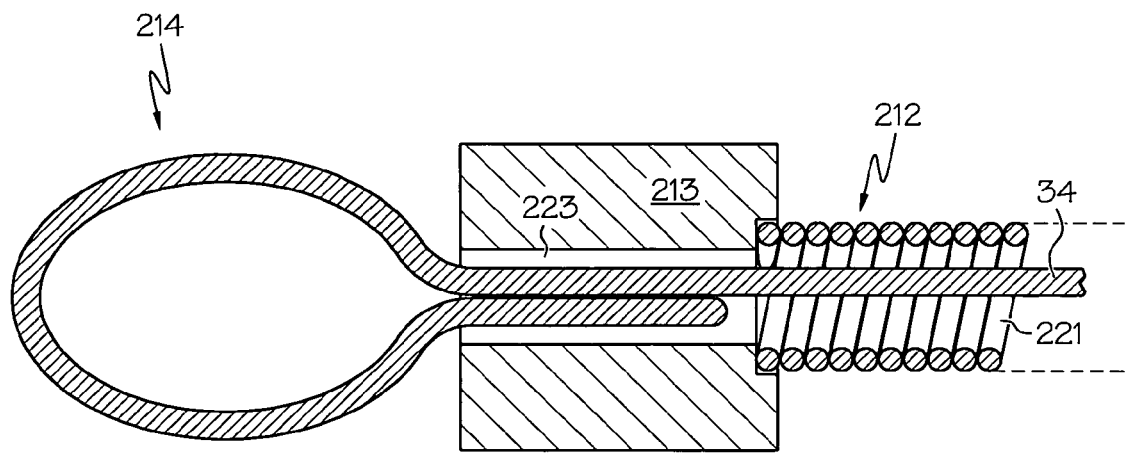
FIG. 12 is a side elevational, cross sectional view of the coupling and a portion of the tube of FIG. 11.
Figure 10:
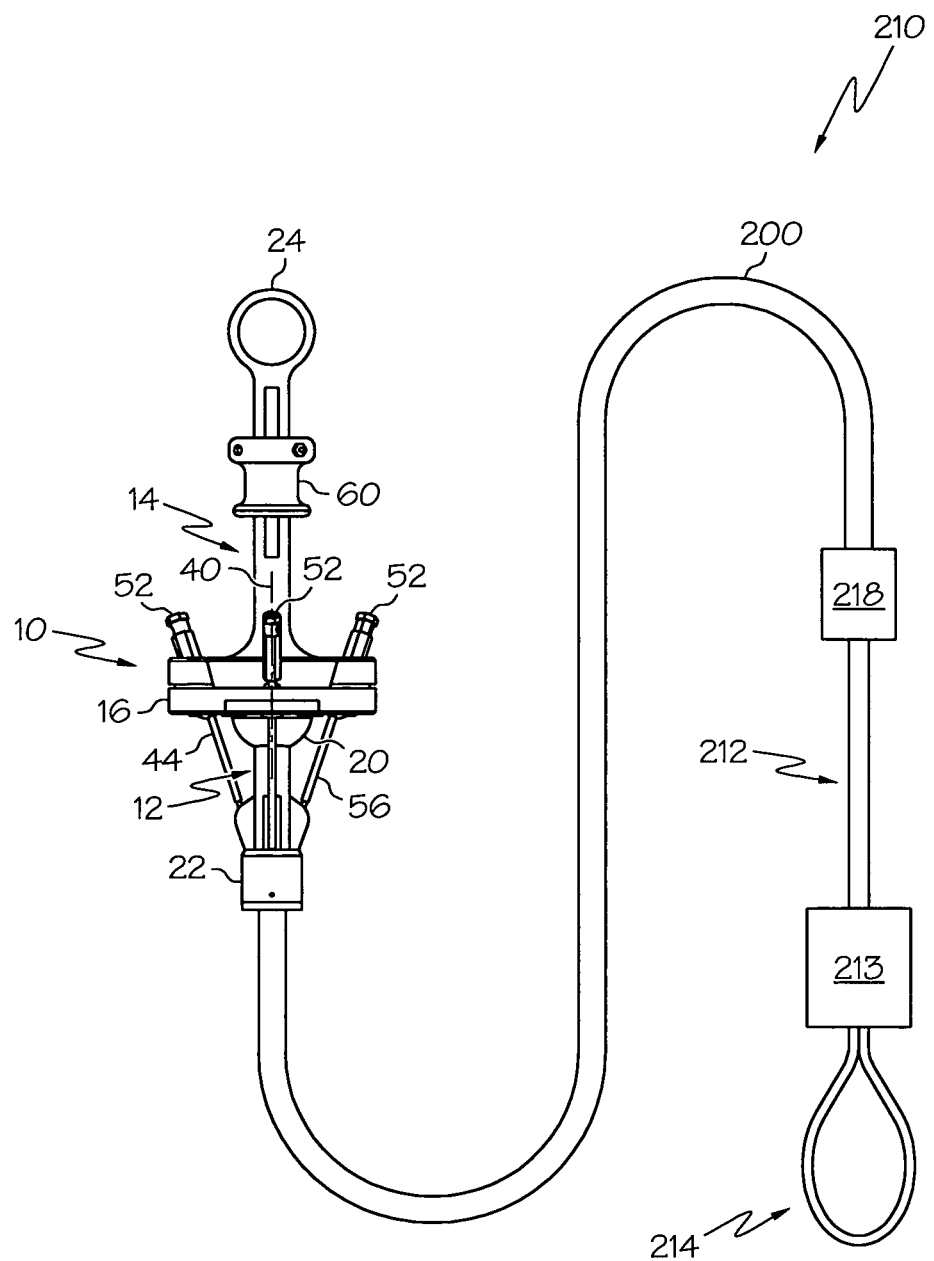
FIG. 10 is a schematic perspective view of a second medical instrument of the invention including the embodiment of the medical instrument handle of FIG. 1, wherein the cables have been omitted for clarity.
Figure 11:
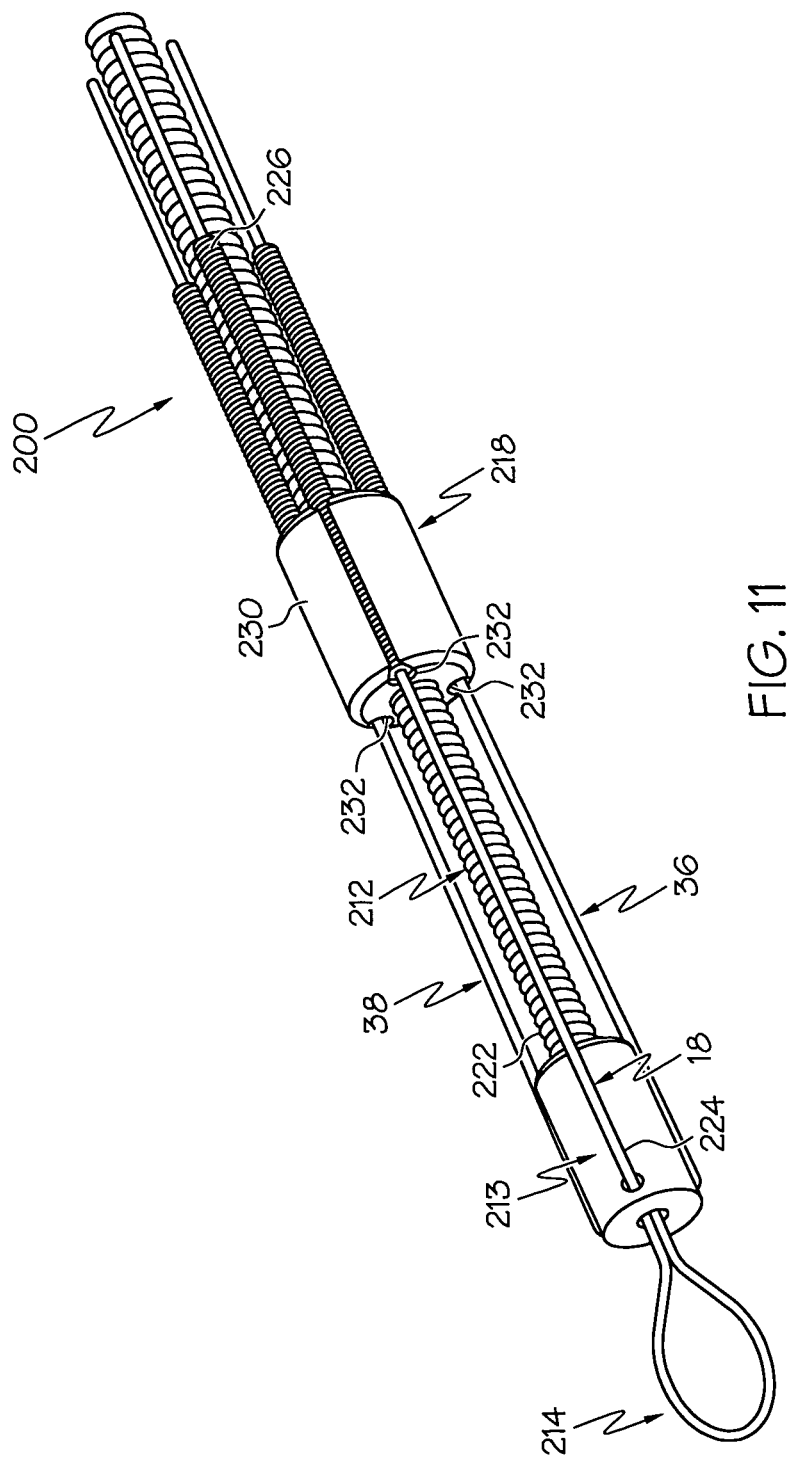
FIG. 11 is an enlarged view of a distal portion of the medical instrument of FIG. 10, wherein pulling of at least one cable articulates a coupling which has a lumen in which a medical end effector is disposable, and wherein the medical end effector is a medical snare.

Referring again to the Figures, FIGS. 10-12 illustrate a second embodiment of the invention, wherein the embodiment of the handle 10 of FIG. 10 is illustrated in more detail in FIGS. 2-7. A first expression of the embodiment of FIGS. 10-12 and 2-7 is for a medical instrument 210 including a flexible tube 212, a coupling 213, a medical end effector 214, an activation wire 34, a fitting 218, a lengthwise translatable first cable 18, and a handle 10. The flexible tube 212 defines a passageway 221 and has a distal tube portion 222 insertable within a patient. The coupling 213 is connected to the distal tube portion 222 and has a lumen 223 in communication with the passageway 221. The medical end effector 214 is disposable in the lumen 223 of the coupling 213. The activation wire 34 is disposable in the passageway 221 and connected to the medical end effector 214. The fitting 218 is spaced apart from, and is disposed proximal to, the coupling 213. The fitting 218 is attached to the tube 212. The first cable 18 is disposed outside the tube 212, is substantially transversely constrained by the fitting 218, and has a distal cable portion 224 connected to the coupling 213. Lengthwise translation of the first cable 18 articulates the coupling 213 (which is a medical instrument member) with respect to the fitting 218. The handle 10 includes a stem 12 and a joystick assembly 14. The stem 12 has a proximal stem portion 20 and a distal stem portion 22. The joystick assembly 14 includes a platform 16, a proximal joystick portion 24 and a distal joystick portion 26, wherein the distal joystick portion 26 is articulatably connected to the proximal stem portion 20. The first cable 18 includes a proximal cable portion 28 which is connected to the platform 16 and which is substantially transversely constrained by the stem 12. Articulation of the joystick assembly 14 with respect to the stem 12 changes a distance 18 between the platform 16 and the stem 12 as measured along the first cable 18. It is noted that such articulation of the joystick assembly 14 results in articulation of the coupling 213 with respect to the fitting 218.

It is noted that an example of a tubular assembly 200 extending from the stem 12 to the fitting 218 is shown in FIG. 10, such tubular assembly 200 being shown in more detail in FIG. 11 wherein it is understood that in FIG. 11 the pipes (such as the first pipe 226) would extend to the stem 12.

In one enablement of the first expression of the embodiment of FIGS. 10-12 and 2-7, the joystick assembly 14 has a joystick lumen 30 and the stem 12 has a stem lumen 32 in communication with the joystick lumen 30. In one variation, the activation wire 34 is disposed in the joystick lumen 30 and in the stem lumen 32.

In a first extension of the first expression of the embodiment of FIGS. 10-12 and 2-7, the medical instrument 210 also includes a lengthwise translatable second cable 36 disposed outside the tube 212, substantially transversely constrained by the fitting 218, and having a distal cable portion 238 attached to the coupling 213. Lengthwise translation of the second cable 36 articulates the coupling 213 with respect to the fitting 118. The second cable 36 includes a proximal cable portion 28 which is connected to the platform 16 and which is substantially transversely constrained by the stem 12. Articulation of the joystick assembly 14 with respect to the stem 12 changes a distance between the platform 16 and the stem 12 as measured along the second cable 36. In one variation, the medical instrument 210 also includes a lengthwise translatable third cable 38 disposed outside the tube 212, substantially transversely constrained by the fitting 218, and having a distal cable portion 238 attached to the coupling 213. Lengthwise translation of the third cable 38 articulates the coupling 213 with respect to the fitting 218. The third cable 38 includes a proximal cable portion 28 which is connected to the platform 16 and which is substantially transversely constrained by the stem 12. Articulation of the joystick assembly 14 with respect to the stem 12 changes a distance between the platform 16 and the stem 12 as measured along the third cable 38. In one modification, the platform 16 has a longitudinal axis 40, and the proximal cable portions 28 of the first, second and third cables 18, 36 and 38 are substantially circularly arrayed 120 degrees apart from each other about the longitudinal axis 40.

In one implementation of the first expression of the second embodiment of FIGS. 10-12 and 2-7, the medical instrument 210 also includes a flexible first pipe 226 surrounding the first cable 18 and attached to the fitting 218, wherein the fitting 218 has a longitudinally-extending circumferential surface 230, wherein the first pipe 226 is disposed in a surface groove 232 (three grooves are shown in FIG. 11) of the circumferential surface 230 of the fitting 218, and wherein the first pipe 226 does not extend distally of the fitting 218. In one variation, the first pipe 226 is a first coil pipe. In one example, the tube 212 is a coil-pipe tube. In one employment, the activation wire 34 is monolithically connected to the medical end effector 214. Thus, in this employment, the activation wire 34 and the medical end effector 214 are two portions of one continuous piece.

Examples, without limitation, of medical end effectors 214 of the first expression of the embodiment of FIGS. 10-12 and 2-7, include a medical snare (as shown in FIGS. 10-12) and include an electrocautery needle knife (not shown). Other examples are left to the artisan. In one example employing the medical snare, the first cable 18 articulates the coupling 213 to a desired orientation, the activation wire 216 is pushed to extend the medical snare out of the distal end of the coupling 213 and around patient tissue (such as a polyp), and the activation wire 34 is then pulled to excise the polyp and retract the medical snare (and polyp) into the distal end of the coupling 213. In one configuration, the medical instrument 210 includes a second cable 36 and a third cable 38 as shown in FIG. 11. In one variation, the handle 10 includes a knob 60 attached to the proximal end of the activation wire 34, wherein the knob 60 surrounds, and is slidably mounted on, the joystick 14, and wherein sliding the knob 60 extends and retracts the snare.

In a third embodiment, not shown, the medical instrument handle 10 is operatively connected to a medical cannula having a first medical cannula tube, a second medical cannula tube, and a resiliently bendable coil spring. The first medical cannula tube has a distal end portion insertable within a patient. The second medical cannula tube is entirely insertable within the patient and is spaced apart from the first medical cannula tube. The coil spring connects the first medical cannula tube to the second medical cannula tube. The medical-instrument-member first articulation cable 18 is located in the first medical cannula tube, has a distal end portion extending from the first medical cannula tube and attached to the second medical cannula tube, and is movable to articulate the second medical cannula tube with respect to the first medical cannula tube. In one example, the first medical cannula tube is an endoscope end cap which is attachable to the distal end of a flexible insertion tube of an endoscope, wherein the second medical cannula tube can be articulated with respect to the first medical cannula tube (and hence with respect to the insertion tube of the endoscope) allowing independent alignment of a wide angle video camera of the endoscope and a medical instrument carried in the second medical cannula tube. In a second example, the first medical cannula tube has a cannula-tube-to-endoscope-rail coupling feature allowing the first medical cannula tube to be coupled to, and slid along, an exterior rail of a flexible insertion tube of an endoscope which also allows independent alignment of a wide angle video camera of the endoscope and a medical instrument carried in the second medical cannula tube. Other examples are left to those skilled in the art.

Several benefits and advantages are obtained from one or more of the expressions of the embodiments of the invention. In a first example, the joystick assembly of the medical instrument handle, with multiple cables, offers intuitive operation of the handle to provide articulation of a medical instrument member (such as, without limitation, a medical end effector or a coupling having a lumen in which a medical end effector is positionable) which is not limited to a single plane.

While the present invention has been illustrated by a description of several expressions of embodiments, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A medical instrument handle comprising:
   a) a stem having a proximal stem portion and a distal stem portion;
   b) a joystick assembly including a platform, a proximal joystick portion and a distal joystick portion, wherein the distal joystick portion is articulatably connected to the proximal stem portion with a ball-and-socket attachment;
   c) a first telescoping conduit extending from the platform to the stem, wherein the first telescoping conduit is connected to the platform by a ball-and-socket connection and to the stem by another ball-and-socket connection; and
   d) a medical-instrument-member first articulation cable extending through the first telescoping conduit and including a proximal cable portion which is connected to the platform and which is substantially transversely constrained by the stem, wherein articulation of the joystick assembly with respect to the stem changes a distance between the platform and the stem as measured along the first articulation cable.

2. The medical instrument handle of claim 1, wherein the joystick assembly has a joystick lumen and wherein the stem has a stem lumen in communication with the joystick lumen, and also including a medical-end-effector activation wire disposed in the joystick lumen and in the stem lumen.

3. The medical instrument handle of claim 2, also including a second telescoping conduit extending from the platform to the stem, wherein the second telescoping conduit is connected to the platform by a ball-and-socket connection and to the stem by another ball-and-socket connection, and a medical-instrument-member second articulation cable extending through the second conduit, the second articulation cable including a proximal cable portion which is connected to the platform and which is substantially transversely constrained by the stem, wherein articulation of the joystick assembly with respect to the stem changes a distance between the platform and the stem as measured along the second articulation cable.

4. The medical instrument handle of claim 3, also including a third telescoping conduit extending from the platform to the stem, wherein the third telescoping conduit is connected to the platform by a ball-and-socket connection and to the stem by another ball-and-socket connection, and a medical-instrument-member third articulation cable extending through the third conduit, the third articulation cable including a proximal cable portion which is connected to the platform and which is substantially transversely constrained by the stem, wherein articulation of the joystick assembly with respect to the stem changes a distance between the platform and the stem as measured along the third articulation cable.

5. The medical instrument handle of claim 4, wherein the platform has a longitudinal axis, and wherein the proximal cable portions of the first, second and third articulation cables are substantially circularly arrayed 120 degrees apart from each other about the longitudinal axis.

6. The medical instrument handle of claim 1, wherein the platform is disposed proximate the distal joystick portion.

7. The medical instrument handle of claim 1, wherein the proximal cable portion has a proximal cable end, wherein the first articulation cable has a first distance between the proximal cable end and the platform, and wherein the first distance is adjustable.

8. A medical instrument comprising:
a) a flexible tube having a distal tube portion insertable within a patient;
b) a medical end effector connected to the distal tube portion;
c) a medical-end-effector activation wire disposed within the tube;
d) a fitting spaced apart from, and disposed proximal to, the medical end effector, wherein the fitting is attached to the tube;
e) a lengthwise-translatable first cable disposed outside the tube, substantially transversely constrained by the fitting, and having a distal cable portion attached to the medical end effector, wherein lengthwise translation of the first cable articulates the medical end effector with respect to the fitting; and
f) a handle including:
(1) a stem having a proximal stem portion and a distal stem portion; and
(2) a joystick assembly including a platform, a proximal joystick portion and a distal joystick portion, wherein the distal joystick portion is articulatably connected to the proximal stem portion with a ball-and-socket attachment; and
(3) a first telescoping conduit extending from the platform to the stem, wherein the first telescoping conduit is connected to the platform by a ball-and-socket connection and to the stem by another ball-and-socket connection,
wherein the first cable extends through the conduit and includes a proximal cable portion which is connected to the platform and which is substantially transversely constrained by the stem, and
wherein articulation of the joystick assembly with respect to the stem changes a distance between the platform and the stem as measured along the first cable.

9. The medical instrument of claim 8, wherein the joystick assembly has a joystick lumen, wherein the stem has a stem lumen in communication with the joystick lumen, and wherein the activation wire is disposed in the joystick lumen and in the stem lumen.

10. The medical instrument of claim 9, also including a second telescoping conduit extending from the platform to the stem, wherein the second telescoping conduit is connected to the platform by a ball-and-socket connection and to the stem by another ball-and-socket connection, and a lengthwise-translatable second cable disposed outside the tube, substantially transversely constrained by the fitting, having a distal cable portion attached to the medical end effector wherein lengthwise translation of the second cable articulates the medical end effector with respect to the fitting, and having a proximal cable portion, extending through the second conduit, which is connected to the platform and which is substantially transversely constrained by the stem, wherein articulation of the joystick assembly with respect to the stem changes a distance between the platform and the stem as measured along the second cable.

11. The medical instrument of claim 10, also including a third telescoping conduit extending from the platform to the stem, wherein the third telescoping conduit is connected to the platform by a ball-and-socket connection and to the stem by another ball-and-socket connection, and a lengthwise-translatable third cable disposed outside the tube, substantially transversely constrained by the fitting, having a distal cable portion attached to the medical end effector wherein lengthwise translation of the third cable articulates the medical end effector with respect to the fitting, and having a proximal cable portion, extending through the third conduit, which is connected to the platform and which is substantially transversely constrained by the stem, wherein articulation of the joystick assembly with respect to the stem changes a distance between the platform and the stem as measured along the third cable.

12. The medical instrument of claim 11, wherein the platform has a longitudinal axis, and wherein the proximal cable portions of the first, second and third articulation cables are substantially circularly arrayed 120 degrees apart from each other about the longitudinal axis.

13. A medical instrument comprising:
a) a flexible tube defining a passageway and having a distal tube portion insertable within a patient;
b) a coupling connected to the distal tube portion and having a lumen in communication with the passageway;
c) a medical end effector disposable in the lumen of the coupling;

d) an activation wire disposable in the passageway and connected to the medical end effector;

e) a fitting spaced apart from, and disposed proximal to, the coupling, wherein the fitting is attached to the tube;

f) a lengthwise-translatable first cable disposed outside the tube, substantially transversely constrained by the fitting, and having a distal cable portion attached to the coupling, wherein lengthwise translation of the first cable articulates the coupling with respect to the fitting; and g) a handle including:
(1) a stem having a proximal stem portion and a distal stem portion; and
(2) a joystick assembly including a platform, a proximal joystick portion and a distal joystick portion, wherein the distal joystick portion is articulatably connected to the proximal stem portion with a ball-and-socket attachment; and
(3) a first telescoping conduit extending from the platform to the stem, wherein the first telescoping conduit is connected to the platform by a ball-and-socket connection and to the stem by another ball-and-socket connection, wherein the first cable extends through the conduit and includes a proximal cable portion which is connected to the platform and which is substantially transversely constrained by the stem, and wherein articulation of the joystick assembly with respect to the stem changes a distance between the platform and the stem as measured along the first cable.

14. The medical instrument of claim 13, wherein the joystick assembly has a joystick lumen, wherein the stem has a stem lumen in communication with the joystick lumen, and wherein the activation wire is disposed in the joystick lumen and in the stem lumen.

15. The medical instrument of claim 14, also including a second telescoping conduit extending from the platform to the stem, wherein the second telescoping conduit is connected to the platform by a ball-and-socket connection and to the stem by another ball-and-socket connection, and a lengthwise-translatable second cable disposed outside the tube, substantially transversely constrained by the fitting, having a distal cable portion attached to the coupling wherein lengthwise translation of the second cable articulates the coupling with respect to the fitting, and having a proximal cable portion, extending through the second conduit, which is connected to the platform and which is substantially transversely constrained by the stem, wherein articulation of the joystick assembly with respect to the stem changes a distance between the platform and the stem as measured along the second cable.

16. The medical instrument of claim 15, also including a third telescoping conduit extending from the platform to the stem, wherein the third telescoping conduit is connected to the platform by a ball-and-socket connection and to the stem by another ball-and-socket connection, and a lengthwise-translatable third cable disposed outside the tube, substantially transversely constrained by the fitting, having a distal cable portion attached to the coupling wherein lengthwise translation of the third cable articulates the coupling with respect to the fitting, and having a proximal cable portion, extending through the third conduit, which is connected to the platform and which is substantially transversely constrained by the stem, wherein articulation of the joystick assembly with respect to the stem changes a distance between the platform and the stem as measured along the third cable.

17. The medical instrument of claim 16, wherein the platform has a longitudinal axis, and wherein the proximal cable portions of the first, second and third articulation cables are substantially circularly arrayed 120 degrees apart from each other about the longitudinal axis.

18. The medical instrument handle of claim 7, wherein the first telescoping conduit has a threaded proximal end portion projecting proximally from the platform, wherein an adjustable nut is threadably attached to the threaded proximal end portion, and wherein the proximal cable end is attached to the adjustment nut.

19. The medical instrument of claim 8, wherein the proximal cable portion has a proximal cable end, wherein the first telescoping conduit has a threaded proximal end portion projecting proximally from the platform, wherein an adjustable nut is threadably attached to the threaded proximal end portion, and wherein the proximal cable end is attached to the adjustment nut, such that the first cable has an adjustable first distance between the proximal cable end and the platform.

20. The medical instrument of claim 13, wherein the proximal cable portion has a proximal cable end, wherein the first telescoping conduit has a threaded proximal end portion projecting proximally from the platform, wherein an adjustable nut is threadably attached to the threaded proximal end portion, and wherein the proximal cable end is attached to the adjustment nut, such that the first cable has an adjustable first distance between the proximal cable end and the platform.

* * * * *